United States Patent [19]

Sander

[11] Patent Number: 5,856,883

[45] Date of Patent: Jan. 5, 1999

[54] ILLUMINATING DEVICE FOR AN OPERATION MICROSCOPE WITH OPTICALLY-MECHANICALLY COUPLED OBSERVER TUBES

[75] Inventor: Ulrich Sander, Oberkochen, Germany

[73] Assignee: Carl-Zeiss Stifting, Brenz, Germany

[21] Appl. No.: 170,400

[22] Filed: Dec. 20, 1993

[30] Foreign Application Priority Data

Dec. 22, 1992 [DE] Germany ................. 42 43 512.9

[51] Int. Cl.⁶ .................... G02B 21/06; A61B 3/10
[52] U.S. Cl. .................. 359/389; 359/385; 351/205
[58] Field of Search .................. 359/385–390, 359/368; 351/205, 211

[56] References Cited

U.S. PATENT DOCUMENTS 4,991,947  2/1991  Sander et al. ........................ 359/389
5,126,877  6/1992  Biber ................................... 359/389
5,140,458  8/1992  Takagi et al. ........................ 359/385
5,270,747  12/1993  Kitajima et al. .................... 351/205

FOREIGN PATENT DOCUMENTS 3208706  11/1982  Germany ............................ 359/385
48808   8/1988  Japan ................................. 359/385

OTHER PUBLICATIONS

Prospect reference No. 30–259.7e.

*Primary Examiner*—Thong Q. Nguyen

[57] ABSTRACT

For optimizing the perception of the red reflex in eye operations, deflecting elements are arranged in the illuminating beam path in the illuminating device of an operation microscope with optically-mechanically coupled observer and co-observer tubes. The deflected illuminating beam pencils overlap, at least partially, the main observer observation beam paths and at least one of the co-observer observation beam paths.

14 Claims, 3 Drawing Sheets

ILLUMINATING DEVICE FOR AN OPERATION MICROSCOPE WITH OPTICALLY-MECHANICALLY COUPLED OBSERVER TUBES

BACKGROUND OF THE INVENTION

1. Field of the Invention

The present invention relates to an illuminating device for an operation microscope with optically-mechanically coupled observer tubes. The operation microscope includes observation tubes for a main observer and a co-observer and a common objective through which observation paths of the main observer and the co-observer pass.

In the use of operation microscopes in surgery, various requirements are set for the illumination of the operation field, according to the medical field of specialization. In micro-surgical operations on the eye, it is usually desired to direct the illuminating light onto the operation field coaxially with the optical axis of the microscope objective. This known kind of illumination has the advantage that the perpendicularly incident light beams are diffusely reflected by the retina. The incident light is thus largely absorbed in the retina. A portion in the red spectral region is reflected, so that the lens capsule, which is the sheathing of the lens, appears to be in a reddish transmitted light due to the returning light. In cataract surgery, tissue residues that have to be aspirated after removal of the lens are made visible at high contrast by this so-called "red reflex." To produce such a red reflex, the illumination pupil and the observation pupil overlap on the retina.

2. Relevant Prior Art

Difficulties now result when such an illuminating device is provided for an operation microscope with optically-mechanically coupled observer tubes. A possible arrangement of an illuminating device of this kind is described in German Patent DE 3,833,876 (U.S. Pat. No. 4,991,947), and in published Document 30-259.7e of Carl-Zeiss-Stiftung of Germany, assignee of the present invention. In this arrangement, the illuminating beam path is deflected by a deflecting element in the direction of the operation field, so that the illuminating beam path runs symmetrically, i.e., coaxial with the optical axis of the main objective. This illuminating arrangement can be selectively inserted. It is termed a "0° illumination" and is responsible for the production of the red reflex. Two further deflecting elements are provided that deflect the illuminating light at a large angle to the optical axis of the main objective in the direction of the operation field. A good contrast of the observed surface structure results for the observer.

In the use of an operation microscope without additional observer tubes for co-observers, it has been found that besides the 0° illumination for producing an extremely homogeneous red reflex, another possible arrangement for the illuminating device is particularly suitable. In this arrangement, an illuminating beam path assumes an angle of about 2° to the optical axis of the main objective.

In operation microscopes without additional observer tubes, in which only two observer pupils pass through the common main objective, the production of such an illumination by a suitable arrangement of a deflecting element is not problematic. However, if a further observer tube is required for a co-observer, a total of four observation pupils then pass through the common main object symmetrically about the optical axis of the main objective. Problems of insufficient space result when arranging one or possibly more deflecting elements near the optical axis of the main objective, for the desired illumination for observing a homogeneous red reflex, such that none of the four observation beam paths is shadowed by the deflecting elements. In spite of this, as homogeneous and contrast-rich red reflex as possible is to be provided for the main observer and co-observers.

SUMMARY OF THE INVENTION

It is the object of the present invention to provide an illuminating device, for an operation microscope with optically-mechanically coupled observer tubes, that provides for the main observer and co-observers as homogeneous and contrast-rich red reflex as possible.

This object is achieved by an illuminating device with at least one illuminating beam path and at least two deflecting elements arranged in the illuminating beam path for deflecting illuminating beam pencils in the illuminating beam path in the direction of object fields. The deflecting elements are arranged in the illuminating beam path such that the illuminating beam pencils, after deflection, overlap, at least partially, the main observer and co-observer observation beam paths.

The illuminating device according to the invention provides the desired illumination for both observers, without substantial shadowing of the observation beam paths for the main observer and the co-observer. The two observers then perceive a homogeneous and contrast-rich red reflex, as was confirmed experimentally.

A suitably selected optical system is arranged in the co-observer beam path, consisting of several individual optical elements, at least one of which is displaceable along the optical axis. As a result, the co-observer has the opportunity for fundus observation. In particular, additional optics that are usual in fundus observation with a contact glass are not required. In fact, the co-observer can observe the fundus without change of equipment.

DESCRIPTION OF THE DRAWINGS

Further advantages and details of the illuminating device according to the invention will become apparent from the following description of the preferred embodiments with reference to the accompanying drawings, which.

DETAILED DESCRIPTION OF PREFERRED EMBODIMENTS

Figure 1:
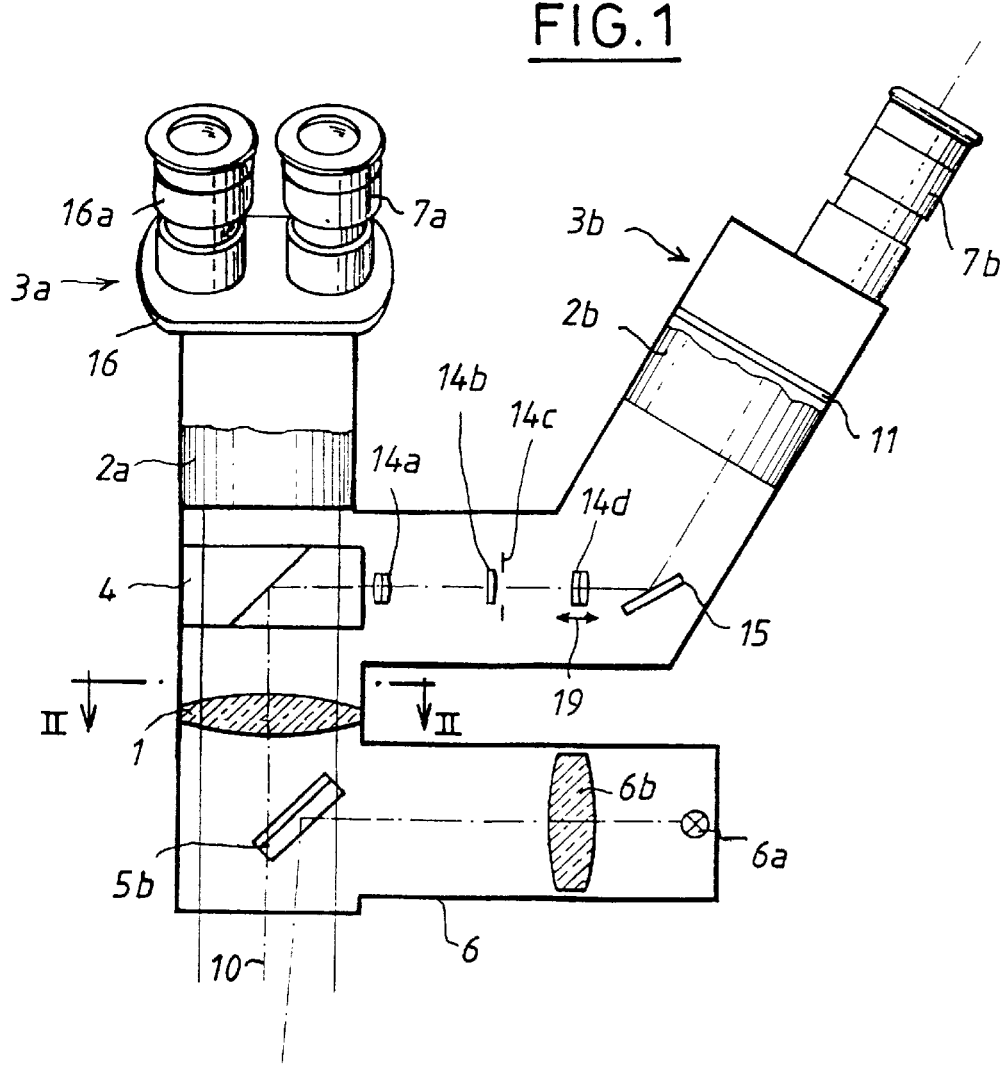
FIG. 1 shows a schematic side view of an operation microscope with optically-mechanically coupled observer tubes, including the illuminating device according to the invention.

An operation microscope having optically-mechanically coupled observer tubes is shown schematically in side view in FIG. 1. In principle, the arrangement of the coupled observer tubes and the construction of the operation microscope correspond to the operation microscope structure described in the cited German Patent DE 3,833,876 (U.S. Pat. No. 4,991,947).

The main observer and co-observer beam paths coming from the object and passing through a common main objective (1) can be deflected or divided by a prism (4) in the direction of the observation tubes (3a, 3b) of the main observer and co-observer. A respective enlarging system (2a, 2b) is arranged between the ocular tubes (7a, 16a, 7b) of the main observer and co-observer observation tubes (3a, 3b) and the prism (4), and selectively provides independently settable enlargements for the main observer and co-observer. The two ocular tubes (7a, 16a, 7b) can be mounted rotatably about interfaces (11) and (16).

An optical system is arranged in the beam path of the co-observer observation tube (3b), and consists of several individual optical elements (14a, 14b, 14d). Starting from the prism (4), there are a first converging optical element (14a) in the form of a cemented element, a field lens (14b) and a second converging optical element (14d) likewise designed as a cemented element. The second optical element (14d), facing the co-observer, is arranged to be displaceable in a defined manner along the optical axis (10), so that it is possible to focus on the fundus (41) of the patient's eye (40).

The optical system (14a, 14b, 14d) in the co-observer's beam path primarily serves to produce an intermediate image by the first converging optical element (14a) in an intermediate image plane (14c). This intermediate image is further imaged by the second converging optical element (14d) in the direction of the co-observer ocular tube, i.e., the optical system (14a, 14b, 14d) acts as a transfer optics. By designing the second optical element (14d) to be displaceable along the optical axis, an opportunity for observing the fundus (41) results. This is an advantageous effect, i.e., the operation microscope according to the invention, with coupled observer tubes, also can be used as a "funduscope" by the co-observer.

A deflecting mirror (15) is arranged in the co-observer observation tube (3b) and deflects the beams coming from the object in the direction of the ocular tube (7b). As an alternative, use of a deflecting prism is, of course, also possible.

An illuminating device (6), preferably of modular construction, is provided, and includes one or more light sources (6a) and imaging optics (6b). Instead of the light source (6a) arranged in the illuminating device (6), the required illuminating light by means of one or more fiber optic light guides and externally located light sources. These preferred embodiments are described below in further detail with reference to FIGS. 3a and 3b.

The schematically shown illuminating device (6) according to FIG. 1 includes at least two deflecting elements (5a, 5b), of which only one is visible in this view. The deflecting elements (5a, 5b) are arranged in front of the portion of the main objective (1) on the object side. The deflecting elements (5a, 5b) are, for example, deflecting mirrors or deflecting prisms or combinations of these. Because of the arrangement of the two deflecting elements (5a, 5b), according to the invention, the illuminating beam pencils of the illuminating device (6), after being deflected, are caused to advantageously overlap, at least partially, the observation beam paths of the main observer and co-observer.

For optimum perception of the red reflex, it is favorable for the illuminating beam pencils to overlap the respective observation beam paths on the retina of the eye, both for the main observer and the co-observer. This is achieved in that the deflecting elements (5a, 5b) are arranged within the illuminating device such that their surfaces projected in the main objective plane are caused to overlap at least partially the two nearest observation pupils that pass through the common main objective (1). In this embodiment, the two illuminating beam pencils each partially overlap one of the observation beam paths of the observer and the respectively like observation beam path of the co-observer. The extent of the overlapping can vary according to the amount of vignetting that is accepted. To achieve such overlapping of the deflected illuminating beam pencils with the adjacent observation beam paths of the main observer and co-observer, the reflecting surfaces of the deflecting elements (5a, 5b) must be arranged slightly tilted about two axes. These two axes are defined by the stereo bases of the main observer and the co-observer. The optical axes of the illuminating beam pencils after they have been deflected, assume in the illustrated arrangement a respective angle of about 5° to the optical axes of the main observer observation beam paths, with reference to the midpoints of the deflecting elements (5a, 5b).

As an alternative to the embodiment shown in FIG. 1, it is possible to arrange the deflecting elements (5a, 5b) between the main objective (1) and the deflecting prism (4).

Figure 2:
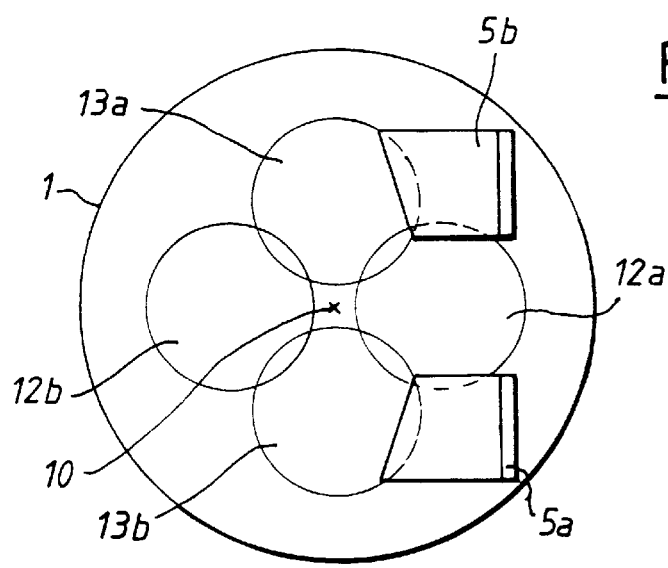
FIG. 2 shows a plan view of the main objective with the observation pupils for the main observer and the co-observer and deflecting elements arranged according to the invention along the lines II—II in FIG. 1.

The arrangement of the deflecting elements (5a, 5b) relative to the observation beam pupils (12a, 12b, 13a, 13b) in the main objective (1) is illustrated by means of FIG. 2. A plan view of the common main objective (1), including a projection of the deflecting elements (5a, 5b) in the plane of the main objective (1), is shown in FIG. 2. A total of four observation pupils or observation beam paths (12a, 12b, 13a, 13b) pass through the main objective (1); two observation pupils (12a, 12b) being associated with the main observer and two observation pupils (13a, 13b) with the co-observer. The two deflecting elements (5a, 5b) are distinguishable in FIG. 2. They deflect the illuminating light in the direction of the object. In the embodiment shown, they are constructed as deflecting mirrors. According to the invention, the two deflecting elements (5a, 5b) are arranged relative to the observation beam paths or observation pupils such that the deflected illuminating beam pencils run adjacent to the observation beam paths of the main observer and co-observer and at least partially overlap these beam paths, especially in the object plane under observation, i.e., the retina being observed. This is achieved by an arrangement in which, as in FIG. 1, the surfaces of the deflecting elements (5a, 5b) projected into the plane of the main objective respectively overlap a main observer observation pupil (12a, 12b) and the respective like co-observer observation pupil (13a, 13b). Moreover, it is important that the overlapping with the main observer pupils and co-observer pupils (12a, 12b, 13a, 13b) is not too large in the plane of the main objective (1). Otherwise, information would be lost for the observers due to shadowing of the observation beam paths by the deflecting elements (5a, 5b).

In addition to the arrangement according to the invention of the deflecting elements that produces a red reflex, it is possible to arrange additional deflecting elements that allow the illuminating light to fall at other angles on the object under observation and provide a good contrast of the observed object field.

Two alternatives to the illuminating device of FIG. 1 are described with reference to FIGS. 3a and 3b. Because of the modular construction of the operation microscope, such alternative illuminating arrangements can be used selectively, i.e., a change of different modules in which the illuminating device is accommodated is always possible. As in FIG. 2, a plan view of the common main objective (1) including the deflecting elements (5a, 5b), is shown. Corresponding to FIG. 2, the same reference numbers are used for the main objective (1), the main observer observation pupils (12a, 12b), the co-observer observation pupils (13a, 13b) and the deflecting elements (5a, 5b).

Figure 3A:
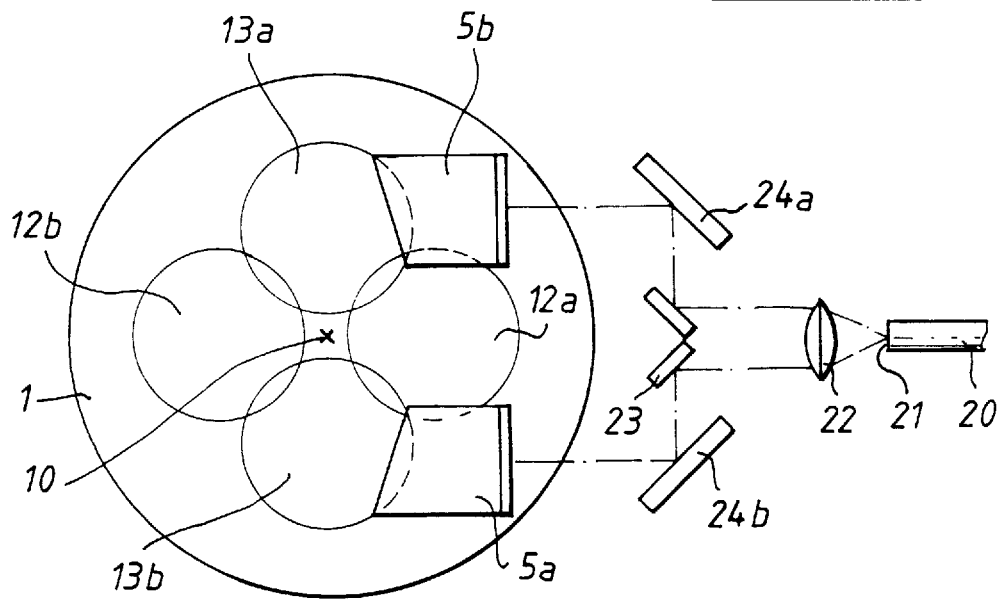
FIG. 3a shows a schematic representation of a second preferred embodiment of the illuminating device with a single light guide.

A single light guide is provided in the embodiment according to FIG. 3a, light from a high power radiation source, not shown, being coupled into it. The illuminating beam pencil, via an optical system (22) arranged following the exit surface (21) of the light guide (20), reaches a beam-splitting optical element (23), which effects a division into two partial beam pencils. Via two deflecting elements (24a, 24b) in the beam paths of the partial beam pencils, the latter reach the deflecting elements (5a, 5b). As described herein above, the deflecting elements (5a, 5b) have a specified arrangement relative to the observation pupils or observation beam paths (12a, 12b, 13a, 13b) and deflect the illuminating light in the direction of the object field. The deflected illuminating beam pencils then run to overlap the observation beam paths of the main observer and the co-observer, or overlap these observation beam paths at least partially. A single illuminating beam pencil is associated with the deflecting elements (5a, 5b) in this embodiment, and is divided into two partial beam pencils.

Figure 3B:
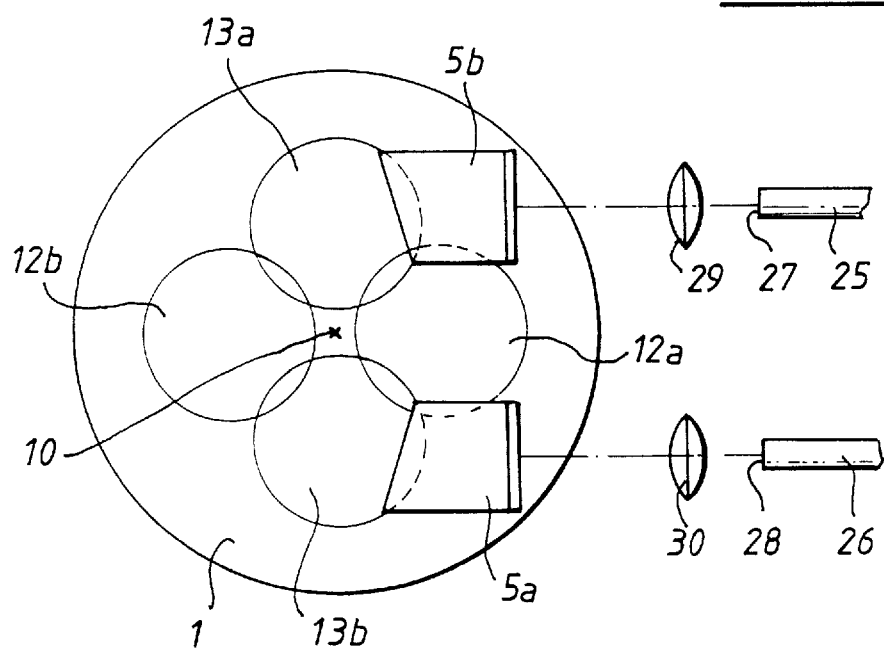
FIG. 3b shows a schematic representation of a third preferred embodiment of the illuminating device with two light guides.

An alternative arrangement is shown in FIG. 3b, in which light from external radiation sources, not shown, is coupled into two light guides (25, 26). Completely separate illuminating beam pencils for each of the two deflecting elements (5a, 5b) are present. An optical system (29, 30) is arranged following the exit surfaces (27, 28) of each light guide. The deflecting elements (5a, 5b) are arranged in the illuminating beam pencils in the manner according to the invention and effect a deflection in the direction of the object field.

In addition, it is possible to arrange suitable stops (50) in FIG. 1 that are geometrically matched to the deflecting elements (5a, 5b) and can be selectively pivoted into the illuminating beam path of the respective deflecting elements and make it possible to block a portion of the illuminating beam pencil incident on the deflecting elements. Such stops (50) are advantageously arranged between the light source (6a) and the deflecting element (5a, 5b). By means of such stops, the fraction of the illuminating light responsible for the red reflex can be set, and especially the fraction of the illuminating beam pencil that overlaps the respective adjacent observation beam path on the retina.

Figure 4:
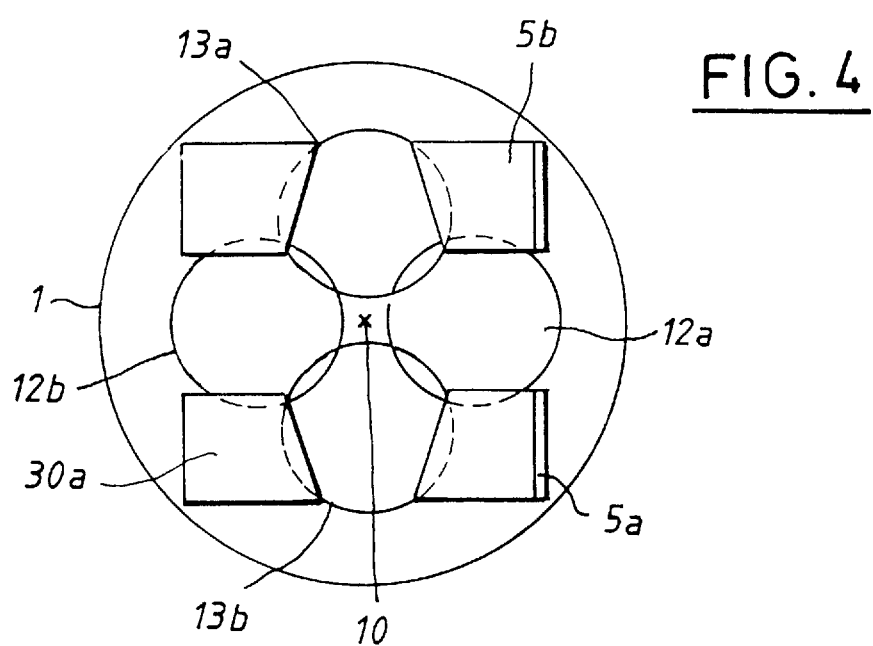
FIG. 4 shows a plan view of the main objective as shown in FIG. 2, with optical beam splitter elements arranged symmetrically to the deflecting elements.

Furthermore, as shown in FIG. 4, two optical beam splitter elements (30a, 30b) are arranged symmetrically to the two deflecting elements (5a, 5b) relative to the optical axis (10) of the main objective (1), so that a given fraction of the light coming from the object can be coupled out into diverse documentation devices, such as cameras or other electro-optical detector units, which can be used to take pictures of the observed operation field for documentation purposes. Such an arrangement is disclosed in U.S. Pat. No. 5,126,877, which issued Jun. 30, 1992 and is owned by Carl-Zeiss-Stiftung, the assignee of the present application. U.S. Pat. No. 5,126,877, is incorporated herein by reference.

I claim:

1. Illuminating device for an operation microscope having optically-coupled observation tubes for a main observer and at least one co-observer and a common objective through which observation beam paths of said main observer and co-observer observation tubes pass, comprising:

at least one illuminating beam path; and at least two deflecting elements arranged side by side in said illuminating beam path for deflecting illuminating beam pencils in said illuminating beam path in a direction of an object field, said deflecting elements each projecting in a common objective plane to overlap at least partly two observation paths of said main observer and said at least one co-observer nearest to said deflecting elements.

2. Illuminating device according to claim 1, wherein said deflecting elements are arranged in said illuminating beam path such that two said illuminating beam pencils, after deflection, overlap at least partially said observation beam paths.

3. Illuminating device according to claim 1, wherein each of said illuminating beam pencils, after deflection, has an angle of about 5° relative to an optical axis of said common objective.

4. Illuminating device according to claim 1, wherein said deflecting elements are arranged in said illuminating beam path such that said illuminating beam pencils, after deflection, each partially overlap at least one main observer observation beam path and a respective like co-observer observation beam path.

5. Illuminating device according to claim 1, wherein said deflecting elements are arranged in front of and on an object side of said common objective.

6. Illuminating device according to claim 1, wherein said deflecting elements comprise deflecting mirrors.

7. Illuminating device according to claim 1, wherein said deflecting elements comprise prisms.

8. Illuminating device according to claim 1, wherein a separate illuminating beam path is associated with each of said deflecting elements.

9. Illuminating device according to claim 8, further comprising a light guide and an optical system positioned following an exit surface of said light guide, wherein each of said illuminating beam pencils is incident upon a deflecting element via said light guide and said optical system.

10. Illuminating device according to claim 1, further comprising a single light guide, an optical system positioned following an exit surface of said light guide, an optical beam splitter element following said optical system for splitting an illuminating beam pencil into two partial beam pencils, and further deflecting elements for deflecting said partial beam pencils onto said two deflecting elements.

11. Operation microscope with an illuminating device according to claim 1, further comprising two optical beam splitter elements arranged symmetrically to said two deflecting elements relative to an optical axis of said common objective, for coupling a given fraction of light coming from said object field to diverse documentation devices.

12. Operation microscope with an illuminating device according to claim 1, further comprising an optical system arranged in said co-observer observation tube, said optical system comprising a first converging optical element for producing an intermediate image in an intermediate image plane, and a second converging optical element in a direction of said co-observer that further images said intermediate image and is displaceable alone an optical axis of said optical system for focusing on a fundus of a patient's eye.

13. Use in eye operations of an operation microscope with an illuminating device according to claim 1.

14. Illuminating device for an operation microscope having optically-coupled observation tubes for a main observer and at least one co-observer and a common objective through which observation beam paths of said main observer and co-observer observation tubes pass, comprising:

at least one illuminating beam path;

at least two deflecting elements arranged side by side in said illuminating beam path for deflecting illuminating beam pencils in said illuminating beam path in a direction of an object field, said deflecting elements each projecting in a common objective plane to overlap at least partly two observation paths of said main observer and said at least one co-observer nearest to said deflecting elements; and further comprising at least one stop geometrically matched to said deflecting elements, said stop being arranged for selectively moving into said illuminating beam path, for stopping out a portion of illuminating light incident on said deflecting elements.

* * * * *